United States Patent
Damodaran

(10) Patent No.: US 6,821,331 B2
(45) Date of Patent: Nov. 23, 2004

(54) PROTEIN-POLYSACCHARIDE HYBRID HYDROGELS

(75) Inventor: Srinivasan Damodaran, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 10/443,603

(22) Filed: May 23, 2003

(65) Prior Publication Data

US 2004/0200386 A1 Oct. 14, 2004

Related U.S. Application Data

(60) Provisional application No. 60/461,552, filed on Apr. 9, 2003.

(51) Int. Cl.$^7$ .............................. C08L 1/28; C08L 3/04; C08L 5/00; C08L 5/04; C08L 5/06; C08L 89/00
(52) U.S. Cl. ................................ 106/135.1; 106/124.3; 106/140.1; 106/140.3; 106/144.1; 106/144.71; 106/145.1; 106/145.5
(58) Field of Search ........................... 106/124.3, 135.1, 106/140.1, 140.3, 144.1, 144.71, 145.1, 145.5

(56) References Cited

U.S. PATENT DOCUMENTS

| | | | |
|---|---|---|---|
| 2,729,628 A | 1/1956 | Mann | |
| 2,923,691 A | 2/1960 | Young et al. | |
| 3,685,998 A | 8/1972 | Miller | |
| 3,720,765 A | 3/1973 | Miller | |
| 4,264,493 A | 4/1981 | Battista | |
| 4,326,052 A | 4/1982 | Kang et al. | |
| 4,326,053 A | 4/1982 | Kang et al. | |
| 4,349,470 A | 9/1982 | Battista | |
| 4,377,636 A | 3/1983 | Kang et al. | |
| 4,385,123 A | 5/1983 | Kang et al. | |
| 4,416,814 A | 11/1983 | Battista | |
| 4,497,930 A | 2/1985 | Yamasaki et al. | |
| 4,572,906 A | * 2/1986 | Sparkes et al. | ................ 514/21 |
| 4,851,521 A | 7/1989 | della Valle et al. | |
| 5,456,745 A | * 10/1995 | Roreger et al. | .......... 106/140.1 |
| 5,462,972 A | 10/1995 | Smith et al. | |
| 5,847,089 A | 12/1998 | Damodaran et al. | |
| 6,235,965 B1 | 5/2001 | Beihoffer et al. | |
| 6,239,230 B1 | 5/2001 | Eckert et al. | |
| 6,310,105 B1 | 10/2001 | Damodaran | |

OTHER PUBLICATIONS

Hwang, D.C. & Damodaran, S. (1997) Synthesis and properties of fish protein–based hydrogel, *J. Amer. Oil Chem. Soc.* 74:1165–1171.

Nagorski, H. (1994) in "Superabsorbent Polymers, Science and Technology," edited by F. Buchholz and N. Peppas, American Chemical Society, Washington, D.C., p. 99.

Robinson, H.W. and Hogden, C.G., (1940) *J. Biol. Chem.* 135:707.

Rocks, J.K., (1971) *Food Technology* 25(5):22–31.

Shungu, D. et al., (1983) *Appl. Environm. Microbiol.* 46:840–5.

Sanderson, G. & Clark, R. (1983) *Food Technology* 37:62–70.

\* cited by examiner

*Primary Examiner*—David Brunsman
(74) *Attorney, Agent, or Firm*—Joseph T. Leone, Esq.; DeWitt Ross & Stevens S.C.

(57) ABSTRACT

Disclosed is a hybrid protein-polysaccharide superabsorbent hydrogel. The hydrogel includes two interpenetrating matrices: a first matrix which is an acylated, cross-linked protein matrix, and a second matrix which is an anionic polysaccharide matrix. The two matrices can be non-cross-linked, or the hydrogel can further include bridging moieties that covalently cross-linking the acylated, cross-linked protein matrix to the anionic polysaccharide matrix.

31 Claims, No Drawings

PROTEIN-POLYSACCHARIDE HYBRID HYDROGELS

CROSS-REFERENCE TO RELATED APPLICATION

Priority is hereby claimed to provisional application Ser. No. 60/461,552, filed Apr. 9, 2003, and incorporated herein by reference.

FEDERAL FUNDING STATEMENT

This invention was made with United States government support awarded by the following agencies: USDA/CSREES 02-CRHF-0-6055. The United States has certain rights in this invention.

FIELD OF THE INVENTION

The present invention relates to protein hydrogels in general and protein-polysaccharide hybrid hydrogels in particular. The hydrogels disclosed herein are capable of absorbing large amounts of water or other liquids per unit mass.

DESCRIPTION OF THE PRIOR ART

Beginning in the early 1970's, and continuing to the present day, there has been a growing awareness that the continued widespread use of non-biodegradable, petroleum-based polymeric materials may pose serious environmental concerns. These concerns are heightened by production statistics showing the enormous and still-growing volume of non-biodegradable plastics produced annually, the vast majority of which are ultimately interred in landfills. This raises concerns not only as to the amount of space available for solid waste disposal (which is disappearing at an increasingly rapid pace), but also raises equally serious concerns that the leaching of toxic monomers and oligomers from landfilled plastics will contaminate ground water, thereby causing health problems in humans and animals.

In addition to concerns regarding human health and the environment, the world-wide depletion of petroleum reserves, in combination with wildly fluctuating petroleum prices due to political and economic conflicts, indicates that less dependence on petroleum-derived products might be prudent. Therefore, the development of alternative, and renewable, resources for industrial products is needed.

Because of the factual and/or perceived economic, environmental, and public health concerns accompanying non-biodegradable, petroleum-based products, a non-petroleum-based, environmentally safe, biodegradable, and renewable source for industrial products is needed. As evidenced by the following references, several types of useful products have been fabricated from renewable sources of starting materials.

For instance, Mann, U.S. Pat. No. 2,729,628, describes a process for increasing the intrinsic viscosity of a long chain polypeptide, particularly natural proteins such as peanut protein, soybean protein, casein, egg albumin, and blood albumin by acylating the protein with terephthalyl dichloride. Here, the protein is reacted with the terephthalyl dichloride using the Schotten-Baumann method at a temperature of from about 0° C. to 30° C.

Young et al., U.S. Pat. No. 2,923,691, describe the polymerization of animal proteins to improve their characteristics for use as animal glue. Young et al. introduce aldehydes to an animal glue protein so as to modify the viscosity and jelly characteristics of the glue product without solidifying or insolubilizing the protein. Here, Young et al. are interested in increasing the viscosity and jelly strength of last run animal glues, which tend to be of inferior quality. The process described by Young et al. includes two steps: first, a cyanic acid salt is reacted with the protein material; second, an aldehyde, such as formaldehyde or glucose, is added to the protein material.

Two patents to Miller (U.S. Pat. Nos. 3,685,998 and 3,720,765), and assigned to the Monsanto Company, describe improved protein feed materials for ruminants. In the Miller patents, protein feeds are rendered resistant to digestive breakdown in the rumen, but not in the abomasum and intestines, by treating protein-containing feed material with a polymerized unsaturated carboxylic acid or anhydride. For instance, the proteinaceous feedstuff is treated with a polyanhydride such as poly(maleic anhydride). This renders the protein feedstuff substantially indigestible in the fluid medium of the rumen, yet still digestible in the acidic media of the abomasum and the intestines. In this manner the proteins of the feedstuff are spared breakdown in the rumen and are available for absorption in the subsequent digestive organs.

Three patent references to Battista (U.S. Pat. Nos. 4,264,493, 4,349,470, and 4,416,814) describe the formation of protein hydrogel structures formed from natural proteins having molecular weights not exceeding 100,000 by dissolving the protein in an aqueous acidic solution, cross-linking the protein, and air drying the solution to a moisture content not exceeding 10 percent. The Battista patents are largely drawn to the formation of clear products such as soft contact lenses, ophthalmological films, and the like.

Although Battista refers to the compositions described therein as hydrogels, that term is defined within the Battista references as meaning "a cross-linked protein polymer of natural origin having an average molecular weight of about 100,000 or less, capable of being swollen by water over a wide range of water contents ranging from as low as 30 percent to 1,000 percent and higher while possessing useful theological control properties for a specific end product uses." The hydrogels described by Battista are not designed to be superabsorbent. Rather, they are designed to be optically clear and to have sufficient mechanical integrity to function as soft contact lenses.

The protein hydrogel structures described in the Battista patents are made from natural protein raw materials that form clear solutions in water. The protein raw material is first dissolved in an acidic aqueous solution of from pH 3.5 to about pH 5.5. A cross-linking agent is then added to the acidic protein solution. Battista's preferred cross-linking agent is Formalin (37% formaldehyde); however, Battista describes other suitable cross-linking agents which may be used, including glutaraldehyde. It must be noted, however, that the Battista patents do not describe acyl-modification of the protein starting material. Nor do the Battista patents describe a superabsorbent protein hydrogel. The protein hydrogels described in the Battista references are designed to have increased wet strength capabilities, thereby enabling their use in soft contact lenses.

Many disadvantages which accompany synthetic hydrogels (such as non-biodegradability) can be overcome by using hydrogels derived from natural polymer sources. In addition to chemically cross-linked protein hydrogels, such as those described by Battista, many proteins can be thermally induced to form gels. The most critical requirements for any type of biopolymer hydrogel are that the gel should have the capacity to absorb a large amount of water relative to its mass upon rehydration, and that the gel material itself should resist dissolution.

However, conventional thermally-induced protein hydrogels do not swell to their original gel volume after they have been dehydrated. This decreased swelling capacity is related to increased hydrogen bonding, as well as electrostatic and hydrophobic interactions which occur in the dehydrated protein. The loss of swelling of thermally-induced protein hydrogels limits their range of industrial applicability.

Perhaps the most desirable of renewable production materials is agricultural biomass. This is due, in large part, to the tremendous amount and variety of agricultural products which are produced in the United States. For instance, biomass (mainly maize) is currently used to produce ethanol for fuel. Fibrous biomass is widely used in the paper and forest products industry. Starch-derived products are also widely utilized in various industrial applications, such as the packing industry, in addition to their use in the food industry.

However, among biopolymers, proteins are perhaps the most under-utilized and under rated in terms of their industrial applications. They are primarily regarded solely as functional and nutritional ingredients in foodstuffs. Their enormous potential as structural elements in non-food industrial applications is largely unrecognized and unrealized. This is unfortunate because proteins offer several distinct advantages over more conventional types of biomass.

For example, unlike polyol-based natural polymers, such as cellulose and other carbohydrates, proteins contain several reactive side groups, including amino, hydroxyl, sulfhydryl, phenolic, and carboxyl moieties. These reactive groups can be used as sites of chemical modification and cross-linking to produce novel polymeric structures.

As a generic class of polymers, hydrogels of all types find high-volume uses in industrial applications, consumer products, and environmental applications. Such applications include diapers, catamenial devices, and industrial absorbents. As used herein, the unqualified term "hydrogel" refers to any naturally-occurring or synthetic material which exhibits the ability to swell in water or some other liquid and to retain a significant fraction of liquid within its structure, but which will not dissolve in the liquid.

Several synthetic hydrogel materials are currently in use. These include such synthetic hydrogels as poly (hydroxyalkyl methacrylates), polyacrylate, poly (acrylamide), poly(methacrylamide) and derivatives thereof, poly(N-vinyl-2-pyrolidone), and poly(vinylalcohol). While these synthetic hydrogel polymers exhibit several interesting properties, their use in industrial, consumer, and environmental applications is less than desirable because of the toxicity of residual monomers and oligomers which are normally present in these gels. Moreover, the poor biodegradability of these synthetic hydrogels also poses the long-term environmental concerns discussed previously.

Most proteins are known to form thermally-induced gels under appropriate conditions. The most critical requirement for any biopolymer to behave as a hydrogel is that it should have the capacity to absorb a large amount of water upon rehydration. As noted earlier, however, in the case of heat-induced protein gels, they do not even swell to their original gel volume once they are dried.

The inability to re-swell is related to increased protein-protein interactions that arise as a result of dehydration. These interactions involve hydrogen bonding, and electrostatic, hydrophobic, and van der Waals forces. It follows then that if these attractive protein-protein interactions are sufficiently weakened and the structure of the polypeptide chain is turned into a more flexible random coil, it should be possible to improve the swelling and water absorbing properties of protein gels. This can, in principle, be achieved through appropriate chemical modification of the side-chain residues. For example, introducing a large number of negative charges, or converting positive charges to negative charges or vice versa, or attaching polyols at critical locations in the polypeptide chain, should increase not only the potential sites for water binding, but also repulsive interactions between protein segments and thus favor protein-solvent instead of protein-protein interactions. The higher the number of charged groups introduced, the higher would be the repulsive interaction and thus the water absorbing properties of the gel. Using this rationale, it is indeed possible to develop protein-based hydrogels having functional properties not found in conventional thermally-induced protein hydrogels.

One of the classes of chemical reagents that has been used for this purpose is ethylenediaminetetraacetic dianhydride (EDTAD):

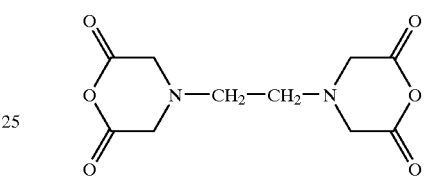

Ethylenediaminetetraacetic Dianhydride (EDTAD)

Reacting EDTAD with the $\epsilon$-amino group of lysine residues in proteins results in formation of an isopeptide derivative as shown below:

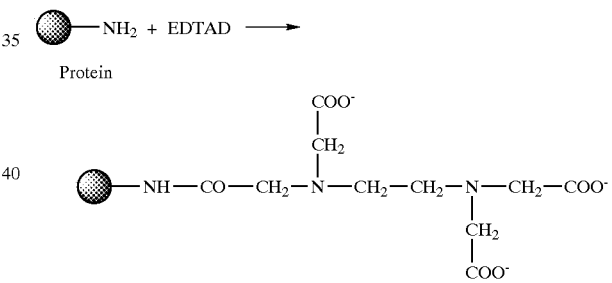

In the above reaction, for each lysyl residue modified (i.e., for each positive charge removed), three negative charges are added to the protein. Thus, a highly polyanionic protein polymer can be synthesized using the above reaction. Cross-linking of the polyanionic polymer by using bifunctional reagents, such as glutaraldehyde, yields an insoluble hydrogel with very high water-absorbing properties.

Recently, it has been shown that chemical modification of soy protein with EDTAD converted the protein into a poly-anionic polymer. When this protein polymer was cross-linked using a bifunctional reagent, the protein was converted into a superabsorbent protein hydrogel. These soy protein hydrogels can absorb 100–350 g water per g of gel, depending on the number of carboxyl groups (i.e., EDTA) attached to the protein. These gels are also capable of absorbing about 13–15 of 0.9% saline solution per g of dry gel within 30 min. They are capable of chelating divalent cations, such as lead, mercury, and cadmium ions. They are completely hydrolyzed by soil microbes within 3–4 weeks, suggesting that they can be composted. See U.S. Pat. No. 5,847,089, to Damodaran & Hwang, and U.S. Pat. No. 6,310,105, to Damodaran.

However, there still exists a need for improved, biodegradable, superabsorbent, biomass-derived hydrogels which exhibit reversible swelling, and which have improved functional qualities, such as absorption under load and centrifugal retention capacity.

SUMMARY OF THE INVENTION

In light of the above-noted shortcoming in the prior art, the present invention is directed to a hybrid protein-polysaccharide hydrogel. In a first embodiment of the invention, the hydrogel comprises two interpenetrating matrices: a first matrix comprising an acylated, cross-linked protein matrix; and a second matrix comprising an anionic polysaccharide matrix. The two matrices are interpenetrating, thereby yielding a homogeneous hydrogel that has superior saline absorption and retention characteristics as compared to hydrogels fabricated solely from protein matrices. In this first embodiment, the protein matrix and the polysaccharide matrix are not cross-linked to one another.

A second embodiment of the invention is drawn to the hydrogel as described in the immediately preceding paragraph, with the hydrogel further comprising bridging moieties that covalently link the acylated, cross-linked protein matrix to the anionic polysaccharide matrix. The bridging moieties may be uniformly dispersed throughout the bulk of the hydrogel gel, or the bridging moieties may be introduced after formation of the non-cross-linked hydrogel so as to form bridging moieties only on the surface of an otherwise non-cross-linked gel particle. In this fashion, each individual particle comprises a core of non-cross-linked hydrogel according to the present invention, enveloped within an outer shell of cross-linked hydrogel according to the present invention.

In either the first or second embodiment of the invention, the protein matrix can be derived from any protein source, without limitation, including biomass, protein isolates derived from biomass, soy bean protein isolate, protein derived from fish protein derived from other animal sources, such as from blood, etc.

The anionic polysaccharide can also be derived from any source, without limitation. By way of example, and not limitation, the anionic polysaccharide can be selected from the group consisting of alginates, carrageenans, carboxylated starches, carboxy-($C_1$–$C_6$-alkyl) cellulose, gellans, hyaluronic acid, pectins, and xanthans. Carboxymethyl cellulose is preferred.

In the preferred method of fabrication, the acylated, cross-linked protein matrix is produced by adding carboxyl moieties to lysyl residues of a protein matrix, to yield an acylated protein matrix, and then crosslinking the acylated protein matrix with a bifunctional cross-linking reagent, to yield the ayclated, cross-linked protein matrix. In the preferred route, carboxyl moieties are added to the lysyl residues of the protein matrix by treating the protein matrix with ethylenediaminetetraacetic acid dianhydride (EDTAD). It is then preferred that the acylated protein matrix is cross-linked using a bifunctional cross-linking reagent selected from the group consisting of

wherein X is an integer of from 2 to 8. Glutaraldehyde is the preferred cross-linking reagent.

To create the bridging moieties in the cross-linked hydrogel, the interpenetrated acylated, cross-linked protein matrix and the anionic polysaccharide matrix are treated with a bifunctional bridging reagent, preferably a diglycidyl ether or ethylene carbonate. This induces the formation of ester bonds linking the carboxyl groups of the protein matrix with the carboxyl groups of the anionic polysaccharide matrix. The preferred bifunctional bridging reagent is a $C_2$–$C_{16}$-alkylene diglycidyl ether and ethylene carbonate, with ethylene glycol diglycidyl ether being the most preferred.

In view of the above discussion, it is a principal aim of the present invention to provide a protein- and polysaccharide-based hydrogel which is superabsorbent, reversibly swellable, biodegradable, and which possesses superior physical characteristics such as absorption under load and centrifugal retention capacity. The hydrogel of the present invention absorbs and retains saline far better than conventional, protein-based hydrogels, thus making the subject hydrogel ideal for use in diapers. The subject hydrogel is also, unlike hydrogels based on synthetic polymers, biodegradeable.

A further aim of the invention is to provide a protein- and polysaccharide-based hydrogel which can be formed from a wide range of protein and polysaccharide starting materials, and which can be used as a substitute for wholly synthetic hydrogels.

The protein from which the subject hydrogel is fabricated can be from any plant or animal source, without limitation. A preferred protein source, its preference derived in large part from its abundance and low cost, is soy-derived protein. Likewise, the polysaccharide from which hydrogel is fabricated can be from any source, without limitation.

In operation, the protein hydrogel can be used wherever high absorption and retention of liquid is desired. Potential end uses for the hydrogels of the present invention include diapers, tampons and menstrual pads, industrial absorbents, spill dams and sealers, drilling muds, ground and waste water reclamation applications, heavy metal sequestration, and the like. These and many other utilities for superabsorbent hydrogels described herein are well within the purview of one of skill in the field of hydrogels.

DETAILED DESCRIPTION OF THE INVENTION

Abbreviations and Definitions

The following abbreviations and definitions are used throughout the specification and claims. Terms not explicitly defined herein retain their standard and accepted definitions within the field of hydrogel fabrication and characterization.

"Anionic Polysaccharide"=This term denotes any anionic polysaccharide, without limitation, including (for example) alginates, carrageenans, carboxylated starches, carboxy-($C_1$–$C_6$-alkyl) cellulose (e.g., carboxymethyl cellulose, carboxethyl cellulose, etc.), gellans, hyaluronic acid, pectins, and xanthans. All are well known in the art and can be obtained commercially. Carboxymethyl cellulose (CMC) is the preferred anionic polysaccharide for use in the present invention.

"AUL"=absorption under load

"Bridging Reagent"=A bifunctional reagent capable of forming a covalent linkage, preferably ester bonds, between carboxyl groups of a protein matrix and carboxyl groups of an anionic polysaccharide matrix. Diglycidyl ethers and ethylene carbonate are preferred.

"CMC"=carboxymethyl cellulose

"CRC"=centrifugal retention capacity

"Cross-Linking Reagent"=A bifunctional reagent capable of cross-linking carboxyl groups within an acylated protein matrix. Dialdehydes are preferred "EGDGE"=ethylene glycol diglycidyl ether, a preferred bridging reagent:

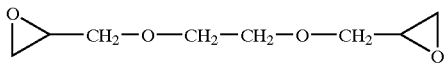

"EC"=ethylene carbonate
"EDTA"=ethylenediaminetetraacetic acid
"EDTAD"=ethylenediaminetetraacetic anydride Commercial Sources: Glutaraldehyde and trinitrobenzenesulfonic acid (TNBS) can be obtained from Sigma Chemical Co., St. Louis, Mo. EDTAD, EC and EGDGE can be obtained from Aldrich Chemical Co., Milwaukee, Wis. Defatted soy flour is a staple that can be acquired from numerous commercial suppliers, including Central Soya Company, Inc, Fort Wayne, Ind. See the remainder of the Detailed Description for other commercial sources.

Introduction

Practical utilization of hydrogels in consumer products such as diapers and catamenial devices depends upon two critical properties: 1) centrifugal retention capacity (CRC) of saline uptake; and 2) saline absorption under load (AUL). The saline uptake capacity of conventional synthetic hydrogels is generally in the range of from about 30 to 35 g saline/g dry hydrogel ("g/g"). In contrast, the saline uptake capacity of conventional protein hydrogels (such as those described in U.S. Pat. No. 5,847,089) is in the range of from about 13 to 15 g/g. The primary factor that limits saline absorption is the number of carboxyl groups per unit mass of the dry gel. As a general proposition, the carboxyl content of a hydrogel and its saline absorption are directly proportional; the higher the carboxyl content, the higher the saline absorption capacity.

In the conventional process of creating protein hydrogels, a protein starting material is converted into a poly-anionic polymer by covalently attaching EDTA to the lysine sidechains of the protein starting material. See Damodaran & Hwang, U.S. Pat. No. 5,847,089, However, because the lysine content of natural proteins is typically in the range of from about 4% to 9%, this places an inherent limit on the number of carboxyl groups that can be incorporated into a hydrogel fabricated entirely from a protein polymer.

The present invention solves this problem by fabricating hydrogel from a combination of proteins and polysaccharides. In short, the invention increases the carboxyl content that can be achieved using a solely protein-based hydrogel by including within the hydrogel matrix an anionic polysaccharide, most preferably carboxymethyl cellulose (CMC). The interpenetrating protein and polysaccharide matrices can be non-cross-linked (referred to herein as "A-type" matrices) or the protein and polysaccharide matrices can be cross-linked by bridging moieties that connect the carboxyl groups of the protein matrix to the carboxyl groups of a polysaccharide matrix (referred to herein as "B-type" matrices). By controlling the extent of cross-linking, the ultimate absorption and retention qualities, including the CRC and AUL, of the resultant hydrogel can be controlled.

The first step of the fabrication process is to modify the protein portion of the matrix with EDTAD, to thereby maximize the carboxyl content of the protein-portion of the protein-polysaccharide hybrid matrix. This step, which maximizes the carboxyl content of the protein portion of the matrix is preferred, but not necessary, when fabricating hydrogels according to the present invention. As a general proposition it is beneficial to maximize the carboxyl content of the protein matrix. However, there are certain industrial application, such as drilling muds, where maximizing carboxyl content may not be necessary or desirable.

As noted above, the source of the protein is largely irrelevant to the functionality of the present invention. Protein from virtually any source (animal-derived, fish-derived, plant-derived, etc.) can be used. Soy protein is preferred because of its abundance and low cost.

By way of illustration (and without limitation), a protein-polysaccharide hydrogel according to the present invention was fabricated by first extracting soy protein from commercial defatted soy flour (Central Soya Company, Inc., Fort Wayne, Ind.). The extraction was accomplished as follows: A 10% dispersion of defatted soy flour in water at pH 10 was stirred for 60 minutes to dissolve the proteins present in the flour. The dispersion was centrifuged at 10,000×g for 10 minutes to remove the insoluble matter. To remove non-protein nitrogen compounds, the pH of the supernatant was adjusted to 4.6 to precipitate the protein. The precipitated protein was recovered by centrifugation at 10,000×g for 10 minutes and re-dissolved in fresh water. Alternative routes for isolating protein from a raw starting material can also be used. For example, soluble non-protein nitrogen compounds can be separated from a solution containing the desired soluble proteins by diafiltration using an ultrafiltration system fitted with a 10,000 kDa nominal molecular weight cut-off membrane.

Chemical modification of proteins with EDTAD may be carried out under the conditions established earlier (Damodaran & Hwang, U.S. Pat. No. 5,847,089), which are the preferred conditions. Briefly, an approximately 1.5% to 2.0% protein solution at pH 11.5 was heated for 15 minutes at 60° C. to dissociate and denature the protein. The solution was then cooled quickly to 20° C. The EDTAD (solid) was then added to the protein solution in several successive small quantities, with continuous stirring between each addition. The solution was stirred until the EDTAD was completely dissolved before adding more EDTAD. The EDTAD reaction was carried out over a period of 1.5 hours. During this reaction period, the pH of the protein solution was kept at a constant value of 11.5 by adding 2 M NaOH using a pH-stat. The total amount of EDTAD used in the reaction was equivalent to about 0.1 g EDTAD/g protein in the solution. Under these reaction conditions about 85–90% of the $\epsilon$-amino groups of lysyl residues present in the protein are modified by EDTAD.

The exact extent of modification was determined by measuring the amount of free $\epsilon$-amino groups present in the protein before and after modification using the trinitrobenzenesulfonic acid (TNBS) method of Hall et at (1973) Analyst, 98:673, which is incorporated herein by reference for its teaching of protein modification analysis. A typical analysis was as follows: To 1 ml of 4% NaHCO$_3$ was added 0.8 ml of a solution containing less than 5 mg EDTAD-treated soy protein isolate, followed by the addition of 0.2 ml of TNBS solution (12.5 mg/ml). The mixture was incubated at 40° C. for 2 hours, and then 3.5 ml of concentrated HCl was added to the mixture. The tube was stoppered and kept at 110° C. for 3 hours, and then cooled. After cooling, the volume was made up to 10 ml with deionized water. The solution was extracted twice with anhydrous diethyl ether. The tube was then unstoppered and heated to 40° C. to allow the residual ether to escape. The absorbance of the yellow $\epsilon$-TNP lysine solution was then measured at 415 nm against a blank. The amount of lysyl residues in the acylated and unacylated soy protein isolate was then determined from a standard curve constructed using lysine.

When treated as described in the preceding paragraphs, about 10–15% of the lysyl residues in the protein are left in the unmodified state. These unmodified lysyl sidechains can then be used in subsequent processing either to cross-link the modified protein with glutaraldehyde to form a cross-linked protein hydrogel or to cross-link the protein with the polysaccharide portion of the matrix. The pH of the modified protein solution was adjusted to about 3.3 to about 3.5 to precipitate the protein. (After modification with EDTAD, the isoelectric point of the protein decreases; in the case described herein, the isoelectric point decreased to about pH 3.3 to 3.5). The protein precipitate was then recovered by centrifugation (10,000×g for 10 minutes).

Type-A and Type-B Hydrogels

The present inventor has discovered that the carboxyl content of protein-based superabsorbent hydrogels can be increased by including an anionic polysaccharide, such as carboxymethyl cellulose (CMC), as an additive in the protein hydrogel matrix. Incorporation of CMC into the cross-linked protein gel matrix can be carried out using two different approaches. In the first approach (the A-Type gel), after thoroughly mixing the EDTAD-modified protein and anionic polysaccharide, the mixture is formed into a homogeneous gel by cross-linking the residual unmodified lysine residues in the protein using a bi-functional crosslinker such as glutaraldehyde. In other words, the protein matrix is cross-linked to itself, and in the process the polysaccharide molecules are entrapped within the cross-linked protein matrix. In this instance, the anionic polysaccharide is physically trapped within the protein gel matrix as an interpenetrating polymer. The anionic polysaccharide is not covalently bonded to the protein, but the two define a homogeneous, interpenetrating polymer network.

In the second approach (the B-Type gel), after mixing the EDTA-modified protein with anionic polysaccharide, and cross-linking the modified protein to itself, the entire system is formed into a homogeneous gel by cross-linking the carboxyl groups of the protein with the carboxyl groups of the anionic polysaccharide using a bifunctional, cross-linking bridging moiety. The bridging reagent used to form the bringing moieties is preferably one that forms ester linkages between the carboxyl groups of the protein matrix and those of the anionic polysaccharide matrix. Diglycidyl ethers, such as $C_2$–$C_{16}$-alkylene diglycidyl ethers are preferred. Ethylene glycol diglycidyl ether (EGDGE) and ethylene carbonate are the most preferred bridging reagents. The cross-linking between the protein matrix and the anionic polysaccharide matrix occurs via formation of ester linkages at both ends of the bifunctional bridging reagent.

Anionic Polysaccharides

As noted in the "Definitions" section, and as used herein, the term "anionic polysaccharide" includes, without limitation, alginates, carrageenans, carboxylated starches, carboxy-$C_1$–$C_6$-alkyl celluloses (such as carboxymethyl cellulose), gellans, hyaluronic acid, pectins, and xanthans.

Alginates are anionic polysaccharides that are salts of alginic acid. Alginic acid is a polyuronide made up of a sequence of two hexuronic acids: β-D-mannuronic acid and α-L-guluronic acid. Alginates are extracted from brown seaweeds and are conventionally used as partially non-thermoreversible gelling and thickening agents in various industries. A wide variety of alginates are commercially available from DeGussa Texturant Systems, Freising, Germany (among many other commerical sources).

Carrageenans are anionic, galactose-containing polysaccharides having a varying degree of sulfonation (generally between about 15% and 40%). Carrageenans are extracted from red seaweeds and are conventionally used as thermoreversible gelling and thickening agents, mainly in the food industry. As the term is used herein, "carrageenan" encompasses fully-refined carrageenan, as well as the semi-refined carrageenan product known as Processed Eucheuma Seaweed or PES. Carrageenans are available from numerous commercial sources, including DeGussa.

Carboxylated starches are natural starches, such as potato starch or corn starch, that have been oxidized or alkyloxi-dized to add carboxyl groups to the starch molecules. "Starch" refers to a carbohydrate polymer occurring in granular form in many plant species, most notably in cereals and tubers, such as corn, wheat, rice, tapioca, potato, etc. Starch polymers are comprised of linked anhydro-α-D-glucose units. Depending on its source, starch may have either a mainly linear structure (amylose) or a branched structure (amylopectin). Carboxylated starches include starch esters and starch ethers. A starch ester is a chemically modified starch in which some of the hydroxyl groups have been replaced by ester groups. Acetylation with acetic anhydride is an example of starch esterification. A starch ether is a chemically modified starch in which some of the hydroxyl groups have been replaced by ether groups. Hydroxypropylation with propylene oxide is an example of starch etherification. Carboxylated starches are available commercially from numerous international suppliers, including National Starch and Chemical Company (Lincolnshire and Chicago, Ill.; a member of the ICI Group of companies).

Carboxy-$C_1$–$C_6$-alkyl celluloses in general, and carboxymethyl cellulose (CMC) in particular, are derivatives of cellulose formed by reacting cellulose with alkali and, for example chloroacetic acid in the case of CMC. The CMC structure is based on the β-(1,4)-D-glucopyranose polymer of cellulose. Different CMC preparations may have different degrees of substitution, the degree of substitution generally falling within the range of from 0.6 to 0.95 derivatives per monomer unit. This substitution is mostly 2-O- and 6-O-linked, followed in order by 2,6-di-O- then 3-O-, 3,6-di-O-, 2,3-di-O-, and lastly 2,3,6-tri-O-linked. CMC molecules adopt an extended, rod-like conformation at low concentrations, but as concentration increases the molecules overlap and adopt a coiled conformation. At high concentrations, CMC molecules entangle to become a thermoreversible gel. CMC dissolves rapidly in cold water and is mainly used for controlling viscosity without gelling. It can be purchased commercially from a host of national and international suppliers, including Aqualon, a wholly-owned subsidiary of Hercules Incorporated, Wilmington, Del.

Gellans have been described in the literature. See, for example, U.S. Pat. Nos. 4,326,052: 4,326,053; 4,377,636; and 4,385,123. Gellans are an extracellular anionic polysaccharide produced by the bacterium *Pseudomonas eloclea* (ATCC 31461). Gellan can be purchased commercially from Merck & Co. (Rahway, N.J.) under the registered trademark GELRITE®. See also Shungu, D. et al. (1983) *Appl. Environm. Microbiol.* 46:840–5; and Sanderson, G. & Clark, R. (1983) *Food Technology* 37:63–70.

Hyaluronic acid (also known as hyaluronan, CAS number: 9067-32-7) is a linear polysaccharide composed of repeating disaccharide units of N-acetyl-glucosamine and D-glucuronic acid. See, for example, U.S. Pat. No. 4,851, 521. The uronic acid and the amino sugar are linked together by alternating β-1,4 and β-1,3 glycosidic bonds. Interestingly, the main source of hyaluronic acid is rooster combs, which contain the polymer at a higher concentration as compared to any other animal tissues tested to date. It is conventionally used as a dietary supplement and has been widely investigated for other medicinal uses. It is available commercially from, for example, The Fidia Group and its wholly-owned subsidiaries and licensees (in the United States, Sanofi-Synthelabo Inc. New York, N.Y.) and from Biolberica (Barcelona, Spain). It is available in bulk quantity, as a highly purified, dry powder, supplied in the form of its sodium salt.

Pectin is a natural component of plants. It is especially abundant in fruit such as apples and citrus. Pectin is associated with cellulose in plant tissues, where it plays a fundamental role in determining their mechanical properties. In plant cells, pectin is linked to cellulose to form protopectin, which has the ability to absorb large amounts of water. Thus, cellulose gives a plant its rigidity, while the pectin components give a plant its flexibility. Pectin has long been used by housewives for gelling jams. It is also available from DeGussa.

Xanthan gum is commonly used as a food modifier. It is an bacteria-derived anionic polysaccharide that is isolated from *Xanthonionas campestris*. See, for example, Rocks, J. K. (1971) *Food Technology* 25(5):22–31. It is available from several international suppliers, including DeGussa.

Centrifugal Retention Capacity

The centrifugal retention capacity (CRC) of hydrogels is determined using the "tea bag" method. (See, for example, Hwang, X.-Q & Damodaran, S. (1997) Synthesis and properties of fish protein-based hydrogel. *J. Amer. Oil Chem. Soc.* 74:1165–1171.) This measurement is defined as the amount of 0.9% saline retained within a hydrogel matrix after the swollen gel has been centrifuged for 5 minutes at 250×g. As noted earlier, the CRC of synthetic hydrogels is in the range of from about 30 to 35 g/g. In contrast, the CRC of current generation soy protein SAP is in the range of from about 13 to 15 g/g, depending on the extent of modification. As discussed earlier, the main factor that limits the saline uptake capacity is the number of carboxyl groups per unit mass of the dry gel.

The procedure for quantitatively measuring the centrifugal retention capacity (CRC) of a hydrogel is straightforward and can be accomplished using common laboratory equipment. The tools required to complete the measurement are as follows:

1. An analytical balance accurate to 0.001 grams (with cover)
2. Paper tea bags (60 mm×85 mm, Paper: Dexter No. 1234 T or equivalent)
3. A heat sealer
4. A timer
5. A large pan (approximately 15 cm deep and large enough to hold several tea bags, volume approximately 5 L)
6. A weighing boat or equivalent
7. A laboratory centrifuge capable of delivering a centrifugal force of 250×g (e.g., 1,400 rpm, using a basket diameter of 225 mm, yields 250×g)
8. 0.9% NaCl saline solution prepared with distilled or deionized water
9. Loose superabsorbent hydrogel samples to be tested, dried The experimental procedure is as follows:

1. Prepare two identical tea bags or use two pre-sealed tea bags.
2. Rotate the sample container end-over-end several times in order to obtain a representative sample of the hydrogel to be tested.
3. Weigh 0.200±0.005 g loose gel (record weight as $W_1$) in a weighing boat and transfer the sample into the tea bag. Heat-seal the open end of the tea bag.
4. Repeat step 3 for the second tea bag. If it takes longer than 5 minutes to prepare the gel-containing tea bags and start the test, place the tea bags in a dessicator.
5. Fill the pan with 0.9% saline. The temperature of the saline should be consistent at about 22±2° C. (This is not required if the test is being completed in a temperature- and humidity-controlled room.) The saline in the pan should be changed after every 6 tea bags per one liter.
6. Hold the gel-containing tea bags horizontally and distribute the gel throughout the tea bag.
7. Gently place the tea bags on the surface of the saline. Allow the tea bags to hydrate for one (1) minute before submerging completely. Assure that entrapped air bubbles are eliminated. Plastic mesh, placed above the tea bags, may help keep the samples submerged.
8. After a soaking period of 30 minutes (±1 minute), remove the tea bags.
9. Place the gel-containing tea bags in the centrifuge basket, in pairs. Position the tea bags in the centrifuge with each tea bag "sticking" to the outer wall of the centrifuge basket. Be careful to evenly space the bags for proper balance when spinning.
10. Close the lid to activate the centrifuge and start the timer after the first revolution. Centrifuge the tea bags for 3 minutes (±10 seconds) at 250×g.
11. Remove the tea bags, weigh each, and record the weights as $W_3$.
12. For each batch of tea bags that were used in the sample analysis, determine the average wet blank weight by taking ten dry, sealed tea bags and perform ing steps 7-11. Record the weight of each wet tea bag and calculate the average wet blank weight (record as $W_2$).

$$\text{Centrifuge Retention Capacity } (g/g) = \{(W_3 - W_2) - W_1\} \div W_1$$

where:
$W_1$=weight of dry sample, in grams
$W_2$=weight of wet blank tea bag (after centrifugation), in grams
$W_3$=weight of wet gel-containing tea bag (after centrifugation), in grams Absorption Under Load (AUL)

Absorption under load (AUL) is a standard test that determines the amount of 0.9% saline that can be absorbed by a 1 g sample of dry hydrogel under an applied pressure of 0.3 psi. The test is described in great detail in H. Nagorski (1994) in "Superabsorbent Polymers, Science and Technology," edited by F. Buchholz and N. Peppas, American Chemical Society, Washington, D.C., p. 99, which is incorporated herein. This test is used widely in the hydrogel industry and is known to those skilled in the hydrogel testing art. The test device comprises a Plexiglas or similarly rigid cylinder (25 mm internal diameter, 50 mm height) having a 400-mesh stainless steel screen disposed in the bottom of the cylinder. The hydrogel sample to be tested (0.156 g) is carefully scattered uniformly on the stainless steel screen. A piston assembly is placed on top of the gel bed and additional weights are placed on the piston so that the pressure on the gel particles is 0.3 psi. The entire device is then weighed accurately. A sintered glass plate is placed in a petri dish and 0.9% NaCl solution is added so that the solution just covers the top of the filter plate. A filter paper is placed on the plate. A filter paper is placed and thoroughly wetted by the saline solution. The Plexiglas device with the sample under load is then placed on top of the filter paper and allowed to sit undisturbed for 1 hour. After 1 hour has elapsed, the device is removed and its entire weight is measured. From these values the mass of saline taken up by one gram of hydrogel is determined.

EXAMPLES

The following Examples are included solely to provide a more complete and consistent disclosure of the hydrogel disclosed and claimed herein. The Examples do not limit the scope of the invention in any fashion.

Example 1

Protein-polysaccharide hybrid hydrogels according to the present invention were prepared as follows:

A-Type Gel: In the case of an A-Type hybrid gel, the pH of EDTAD-modified soy protein precipitate (prepared as described hereinabove) was carefully adjusted to pH 9.0 by drop-wise addition of 4N NaOH with continuous mixing. A 5% dispersion of CMC in water (commercial-grade and having a viscosity in the range of from about 3,000 to about 6,000 cp at 1%) was pre-equilibrated to form a transparent viscous gel. A calculated amount of this CMC gel was added to the EDTAD-modified protein gel so that the CMC-to-protein ratio in the mixture was from about 1:20 to about 1:10 (g/g). The protein concentration of the mixture was determined by the biuret method (Robinson, H. W. and C. G. Hogden (1940) *J. Biol. Chem.* 135:707) and adjusted to 12% (w/w) by adding the required amount of water. The mixture was then thoroughly blended using a kneading-type blender in order to completely mix the CMC into the protein gel matrix. By thoroughly mixing the modified protein gel and the CMC, an interpenetrating polymer network was formed at the molecular level between the modified protein and the CMC.

A calculated amount of a 10% aqueous solution of glutaraldehyde was, added to the gel described in the immediately preceding paragraph so that the ratio of glutaraldehyde-to-protein in the mixture was in the range of from about 1:50 to about 1:200 (w/w). The sample was thoroughly mixed and cured overnight to set into a cross-linked gel network.

The resulting gel was dehydrated by treatment with absolute ethanol (×3). In addition to effecting dehydration, the ethanol treatment further denatured the protein in situ in the cross-linked gel network. This significantly improved saline and water uptake properties of the resultant hydrogel (described below). The dehydrated gel was de-solventized by incubating at 40° C. under vacuum overnight. The dried gel was ground and sized to ~500 micron size using standard sieves. The CRC of saline uptake of the gel was determined as described herein.

B-Type gels were prepared from A-Type gels as described in Example 13

Example 2

A soy protein solution (1,500 mL volume, 1.465% protein) was reacted with 3.3 g EDTAD under the conditions described above. The EDTA-modified protein dispersion (15% w/w) was thoroughly mixed with 1.1 g CMC pre-swollen in 30 mL water using a "POLYTRON"-brand homogenizer. The pH of the mixture was adjusted to 9.0. One (1) mL of 10% glutaraldehyde solution was added to the protein-CMC mixture and mixed well. The sample was cured overnight at room temperature, followed by ethanol treatment (×3). The sample was finally dried at 40° C., ground with a mortar and pestle and sized to 350 to 750 microns using standard sieves.

Example 3

One (1) kg of fresh carp fish was homogenized at pH 12 and left to stand for 20 to 30 min. The slurry was centrifuged at 10,000×g for 15 min. The supernatant was collected and adjusted to pH 4.6 to precipitate the protein. The slurry was centrifuged at 7,000×g for 10 min. The protein pellet was re-dispersed in water at pH 4.6 and then centrifuged at 7,000×g for 10 min. The protein pellet was collected and dissolved in water at pH 11.5 to a final concentration of 1.13%. A 4.5 L sample of this fish protein solution was reacted with 11.2 g of EDTAD at ambient temperature as described above. To a 15% dispersion of this modified protein was added 2.5 g CMC pre-swollen in 65 mL water and the resultant mixture thoroughly homogenized. The pH of the dispersion was adjusted to 9.0. The sample was cross-linked with glutaraldehyde at a glutaraldehyde to protein ratio of 1:200 w/w. The sample was cured overnight at room temperature, followed by ethanol treatment. The sample was finally dried at 40° C., ground with a mortar and pestle and sized to 350 to 750 microns using standard sieves.

Example 4

A sample (4.5 L) of fish protein solution (0.95%, prepared as in Example 3) was reacted with 10 g of EDTAD at 10° C. as described above. To a 15% dispersion of this modified protein was added 2.1 g CMC pre-swollen in 55 mL water and homogenized. The pH of the dispersion was adjusted to 9.0. The sample was cross-linked with glutaraldehyde at a glutaraldehyde to protein ratio of 1.100 w/w. The sample was cured overnight at room temperature, followed by ethanol treatment (×3). The sample was finally dried at 40° C., ground with a mortar and pestle and sized to 350 to 750 microns using standard sieves.

Example 5

A sample (4.0 L) of fish protein solution (0.77%, prepared as in Example 3) was reacted with 6.8 g of EDTAD at ambient temperature as described above. To a 15% dispersion of this modified protein was added 2.1 g CMC pre-swollen in 55 mL water and homogenized. The pH of the dispersion was adjusted to 9.0. The sample was cross-linked with glutaraldehyde at a glutaraldehyde to protein ratio of 1:100 w/w. The sample was cured overnight at room temperature, followed by ethanol treatment (×3). The sample was finally dried at 40° C., ground with a mortar and pestle and sized to 350 to 750 microns using standard sieves.

Example 6

A sample (11.7 L) of soy protein solution (1.0%) was reacted with. 14.2 g of EDTAD at ambient temperature as described above. To a 15% dispersion (133 g) of this modified protein was added 2.0 g CMC pre-swollen in 50 mL water and the resultant mixture homogenized. The pH of the dispersion was adjusted to 9.0. The sample was cross-linked with glutaraldehyde at a glutaraldehyde to protein ratio of 1:100 w/w. The sample was cured overnight at room temperature, followed by ethanol treatment (×3). The sample was finally dried at 40° C., ground with a mortar and pestle, and sized to 350 to 750 microns using standard sieves.

Example 7

A sample (20 g) of blood plasma protein was dissolved in 500 mL water and heated at 75° C. for 30 min. The pH was adjusted to 5.2 to precipitate the protein. The slurry was centrifuged at 7,000×g for 10 min. The protein pellet was dissolved in 1.5 L water at pH 12. The final protein concentration was 0.83%. The protein solution was reacted with 2.86 g EDTAD at pH 11.5 over a period of 1.5 h. About 11.3 g of the modified protein was dissolved in water to a final concentration of 15%. To this was added about 1.5 g of CMC pre-swollen in 40 mL water and homogenized. The sample was cross-linked with glutaraldehyde at a glutaraldehyde to protein ratio of 1:200. The sample was cured overnight at room temperature, followed by ethanol treatment (×3). The sample was finally dried at 40° C., ground with a mortar and pestle and sized to 350 to 750 microns using standard sieves.

Example 8

A sample (10 g) of blood plasma protein was dissolved in 110 mL water and dialyzed against water for 4 h. The solution was then diluted to 716 mL, resulting in a final protein concentration of 1.2%. The protein solution was reacted with 1.7 g EDTAD at pH 11.5 over a period of 1.5 h. To a 15% solution (8.6 g protein) of the modified protein was added 0.86 g of CMC pre-swollen in 40 mL water and the resulting mixture thoroughly homogenized. The sample was cross-linked with glutaraldehyde at a glutaraldehyde to protein ratio of 1:200. The sample was cured overnight at room temperature, followed by ethanol treatment. The sample was finally dried at 40° C., ground, and sized to 350 to 750 micron size using standard sieves.

Example 9

A sample (50 g) of blood plasma protein was dissolved in 2.5 L water at pH 11.8. The final protein concentration was 1.68%. The protein solution was reacted with 8.5 g EDTAD at pH 11.5 over a period of 1.5 h. About 35 g of the modified protein was dissolved in water to a final concentration of 15%. To this was added about 3.5 g of CMC pre-swollen in 40 mL water and the resulting mixture homogenized. The sample was cross-linked with glutaraldehyde at a glutaraldehyde to protein ratio of 1:200. The sample was cured overnight at room temperature, followed by ethanol treatment. The sample was finally dried at 40° C., ground and sized to 350 to 750 microns using standard sieves.

Example 10

A sample (50 g) of blood plasma protein was dissolved in 110 mL water and dialyzed overnight against water. The solution was then diluted to a final protein concentration of 2.14% (1.6 L total volume). The protein solution was reacted with 6.8 g EDTAD at pH 11.5 over a period of 1.5 h. To a 15% solution (34.2 g protein) of the modified protein was added 4.1 g of CMC pre-swollen in 100 mL water and the resulting mixture homogenized. The sample was cross-linked with glutaraldehyde at a glutaraldehyde to protein ratio of 1:100. The sample was cured overnight at room temperature, followed by ethanol treatment. The sample was finally dried at 40° C., ground and sized to 350 to 750 microns size using standard sieves.

Example 11

A sample (12.0 L) of soy protein solution containing 124.9 g soy protein was reacted with 18.7 g of EDTA, at ambient temperature as described above. To a 15% dispersion (133 g) of this modified protein was added 12.5 g CMC pre-swollen in 300 mL water and the resulting mixture homogenized. The pH of the dispersion was adjusted to 9.0. The sample was cross-linked with glutaraldehyde at a glutaraldehyde to protein ratio of 1:100 w/w. The sample was cured overnight at room temperature, followed by ethanol treatment. The sample was finally dried at 40° C., ground with a mortar and pestle, and sized to 350 to 750 microns using standard sieves.

Example 12

The CRC values for each of the gels prepared in Examples 2 through 11 were determined as described hereinabove. Table 1 shows CRC values of these protein-CMC hybrid hydrogels:

TABLE 1

CRC of Various Protein-CMC Hybrid Hydrogels

| Experiment | Protein type | Control | +5% CMC | +10% CMC |
|---|---|---|---|---|
| Example 2 | Soy protein | 13.15 | 19.72 | |
| | Soy protein | 12.85 | 20.06 | |
| Example 3 | Fish protein | 14.70 | 20.62 | |
| Example 4 | Fish protein | 11.0 | 16.3 | |
| | | 17.68 | 21.43 | |
| Example 5 | Fish protein | 9.95 | | 16.4 |
| Example 6 | Soy protein | 10.27 | | 14.54 |
| Example 7 | Blood Plasma protein | | | 14.54 |
| Example 8 | Blood Plasma protein | 15.43 | | 19.63 |
| Example 9 | Blood Plasma protein | 13.86 | | 18.4 |
| Example 10 | Blood Plasma protein | 14.36 | | 19.4 |
| Example 11 | Soy protein | 13.68 | | 21.96 |

The "controls" were cross-linked protein hydrogels lacking any added CMC. As can be seen from the CRC values presented in Table 1, protein-polysaccharide hydrogels prepared according to the present invention have markedly improved CRC values as compared to hydrogels containing solely a protein matrix.

Example 13

Absorption under load (AUL) is typically defined as the amount (g/g) of saline uptake by the hydrogel under a constant static pressure of 0.3 psi. The AUL of synthetic polyacrylate-based hydrogels is in the range of from about 20 to 25 g/g at 0.3 psi. This compares with an AUL of about 5 to 6 g/g for soy protein-based hydrogels.

Surface cross-linked hydrogels according to the present invention were made as follows: Samples (about 2 g each) of the dried protein-CMC hydrogel particles described in Example 1 (B-Type) (300 to 500 micron) were fluidized using a stirrer. Stock solutions of EGDGE in the concentration range of from 20 to 80% in 50% aqueous ethanol were made. The fluidized dried gel particles were coated uniformly by drop-wise addition of 100 μL of the EGDGE stock solution. The fluidized state of the particles is necessary to ensure uniform coating of the particles with the cross-linker. Under these conditions, evaporation of ethanol leaves a thin film of the cross-linker on the surface of the gel particles; the cross-linker does not migrate deep into the particle. The weight ratio of cross-linker to gel particle was varied by spraying 100 μL of EGDGE stock solutions containing 20 to 80% EGDGE. For example, when 100 μL of 20% EGDGE was sprayed on 2 g of gel particles, after drying, the EGDGE to gel ratio is 1%. However, this 1% EGDGE is localized only on the surface of the particle, which, when cross-linked, forms a strong surface film. The coated gel particles were baked at 140° C. for various time intervals ranging from 10 min to 3 h. Samples were also prepared with ethylene carbonate (EC) as the surface cross-linker, using the above-described conditions.

The AUL of the surface cross-linked samples was be determined using a standard method described by Nagorski (1994), supra and outlined hereinabove. Briefly recapping, the test device is a Plexiglas cylinder (25 mm internal diameter, 50 mm height) with a 400 mesh stainless steel screen glued in the bottom. Each hydrogel sample (0.156 g)

was scattered uniformly on the stainless steel screen. A piston assembly was placed on top of the gel bed and additional weights were placed on the piston so that the pressure on the gel particles was 0.3 psi. The entire device was then weighed accurately. A sintered glass plate was placed in a petri dish and 0.9% NaCl solution was added in sufficient amount to cover the top of the filter plate. A filter paper was placed on the plate and thoroughly wetted by the saline solution. The Plexiglas device with the sample under 0.3 psi load was then placed on top of the filter paper. Each sample was allowed to rest in this position for 1 h. After 1 h, the device was removed from the saline and its entire weight was determined. By comparing the initial weight of the device loaded with the dry gel and the final weight of the device after 1 hour of saline uptake, the mass of saline taken up by one gram of hydrogel was determined for each sample.

Table 2 shows AUL of protein-CMC hydrogels prepared under various conditions.

TABLE 2

AUL of Soy Protein-CMC Hybrid Hydrogels

| % surface cross-linker | Incubation time at 140° C. | AUL (0.3 psi) g/g |
| --- | --- | --- |
| 1% EGDGE | 3 h | 9.8 |
| 2% EGDGE | 3 h | 8.7 |
| 3% EGDGE | 3 h | 8.05 |
| 2% EGDGE | 10 min | 12.4 |
| 3% EC | 1 h | 9.55 |
| 4% EC | 1 h | 9.55 |
| 4% EC | 2 h | 9.00 |
| 3% EC | 3 h | 8.52 |
| 4% EC | 3 h | 8.70 |

As can be seen from the values presented in Table 2, the hydrogels, produced according to the subject invention have distinctly improved AUL values (ranging from 8.05 to 12.4 g/g as compared to soy protein-based hydrogels, which exhibit AUL values ranging from about 5 to 6 g/g. Thus, the protein-polysaccharide hydrogels according to the present invention can absorb more saline, on a per gram basis, than soy protein-based hydrogels.

What is claimed is:

1. A protein-polysaccharide hydrogel comprising:

an acylated, crosslinked protein matrix; and an anionic polysaccharide matrix interpenetrating with the acylated, cross-linked protein matrix.

2. The hydrogel of claim 1, wherein the acylated, cross-linked protein matrix comprises a protein derived from biomass.

3. The hydrogel of claim 1, wherein the acylated, cross-linked protein matrix comprises a protein isolate derived from biomass.

4. The hydrogel of claim 1, wherein the acylated, cross-linked protein matrix comprises soy bean protein isolate.

5. The hydrogel of claim 1, wherein the acylated, cross-linked protein matrix, comprises a protein derived from fish.

6. The hydrogel of claim 1, wherein the anionic polysaccharide is selected from the group consisting of alginates, carrageenans, carboxylated starches, carboxy-($C_1$-$C_6$-alkyl) cellulose, gellans, hyaluronic acid, pectins, and xanthans.

7. The hydrogel of claim 1, wherein the anionic polysaccharide is carboxymethyl cellulose.

8. The hydrogel of claim 1, wherein the acylated, cross-linked protein matrix is produced by:

adding carboxyl moieties to lysyl residues of a protein matrix, to yield an acylated protein matrix: and then cross-linking the acylated protein matrix with a bifunctional cross-linking reagent, to yield the ayclated, cross-linked protein matrix.

9. The hydrogel of claim 8, wherein the carboxyl moieties are added to the lysyl residues of the protein matrix by treating the protein matrix with ethylenediaminetetraacetic acid dianhydride.

10. The hydrogel of claim 8, wherein the acylated protein matrix is cross-linked using a bifunctional cross-linking reagent selected from the group consisting of $$OCH-(CH_2)_x-CHO$$

wherein X is an integer of from 2 to 8.

11. The hydrogel of claim 8, wherein the bifunctional cross-linking reagent is glutaraldehyde.

12. The hydrogel of claim 1, further comprising bridging moieties covalently linking the acylated, cross-linked protein matrix to the anionic polysaccharide matrix.

13. The hydrogel of claim 12, wherein the bridging moieties are produced by treating the interpenetrated acylated, cross-linked protein matrix and the anionic polysaccharide matrix with a bifunctional bridging reagent.

14. The hydrogel of claim 13, wherein the bifunctional bridging reagent is a diglycidyl ether or ethylene carbonate.

15. The hydrogel of claim 13, wherein the bifunctional bridging reagent is a $C_2$-$C_{16}$-alkylene diglycidyl ether.

16. The hydrogel of claim 13, wherein the bifunctional bridging reagent is ethylene glycol diglycidyl ether or ethylene carbonate.

17. A protein-polysaccharide hydrogel comprising an acylated, cross-linked protein matrix;

an anionic polysaccharide matrix interpenetrating with the acylated, cross-linked protein matrix; and bridging moieties covalently linking the acylated, cross-linked protein matrix to the anionic polysaccharide matrix.

18. The hydrogel of claim 17, wherein the acylated, cross-linked protein matrix comprises a protein derived from biomass.

19. The hydrogel of claim 17, wherein the acylated, cross-linked protein matrix comprises a protein isolate derived from biomass.

20. The hydrogel of claim 17, wherein the acylated, cross-linked protein matrix comprises soy bean protein isolate.

21. The hydrogel of claim 17, wherein the acylated, cross-linked protein matrix comprises a protein derived from fish.

22. The hydrogel of claim 17, wherein the anionic polysaccharide is selected from the group consisting of alginates, carrageenans, carboxylated starches, carboxy-($C_1$-$C_6$-alkyl) cellulose, gellans, hyaluronic acid, pectins, and xanthans.

23. The hydrogel of claim 17, wherein the anionic polysaccharide is carboxymethyl cellulose.

24. The hydrogel of claim 17, wherein the acylated, cross-linked protein matrix is produced by:

adding carboxyl moieties to lysyl residues of a protein matrix, to yield an acylated protein matrix: and then cross-linking the acylated protein matrix with a bifunctional cross-linking reagent, to yield the ayclated, cross-linked protein matrix.

25. The hydrogel of claim 24, wherein the carboxyl moieties are added to the lysyl residues of the protein matrix by treating the protein matrix with ethylenediaminetetraacetic acid dianhydride.

26. The hydrogel of claim 24, wherein the acylated protein matrix is cross-linked using a bifunctional cross-linking reagent selected from the group consisting of

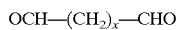

OCH—(CH$_2$)$_x$—CHO wherein X is an integer of from 2 to 8.

27. The hydrogel of claim 24, wherein the bifunctional cross-linking reagent is glutaraldehyde.

28. The hydrogel of claim 17, wherein the bridging moieties are produced by treating the interpenetrated acylated, cross-linked protein matrix and the anionic polysaccharide matrix with a bifunctional bridging reagent.

29. The hydrogel of claim 28, wherein the bifunctional bridging reagent is a diglycidyl ether or ethylene carbonate.

30. The hydrogel of claim 28, wherein the bifunctional bridging reagent is a $C_2$–$C_{16}$-alkylene diglycidyl ether.

31. The hydrogel of claim 28, wherein the bifunctional bridging reagent is ethylene glycol diglycidyl ether or ethylene carbonate.

* * * * *